United States Patent
Yamamoto et al.

(10) Patent No.: US 7,029,670 B2
(45) Date of Patent: Apr. 18, 2006

(54) MEDICINES FOR RELIEVING INTESTINAL DISORDERS

(75) Inventors: Naoyuki Yamamoto, Sagamihara (JP); Osamu Masuda, Yokohama (JP); Kyouko Kaneko, Tokyo (JP); Nagisa Ikeda, Tokorozawa (JP); Yuu Ishida, Tokyo (JP); Daisuke Kusuda, Tokyo (JP); Tadashi Shinoda, Sagamihara (JP)

(73) Assignee: Calpis Co., Ltd., Tokyo (JP)

( * ) Notice: Subject to any disclaimer, the term of this patent is extended or adjusted under 35 U.S.C. 154(b) by 0 days.

(21) Appl. No.: 10/250,382

(22) PCT Filed: Dec. 25, 2001

(86) PCT No.: PCT/JP01/11347

§ 371 (c)(1),
(2), (4) Date: Jun. 26, 2003

(87) PCT Pub. No.: WO02/053163

PCT Pub. Date: Jul. 11, 2002

(65) Prior Publication Data

US 2004/0096434 A1 May 20, 2004

(30) Foreign Application Priority Data

Dec. 28, 2000 (JP) ........................................ 2000-401035

(51) Int. Cl.
*A01N 63/00* (2006.01)
*C12N 1/20* (2006.01)

(52) U.S. Cl. ................ 424/93.45; 435/252.9; 435/78.01; 514/892

(58) Field of Classification Search ............... 424/93.45; 435/252.9, 78.01, 68.1; 514/892; 426/34, 426/42, 43, 46
See application file for complete search history.

(56) References Cited

U.S. PATENT DOCUMENTS

| | | | |
|---|---|---|---|
| 3,846,560 A | 11/1974 | Hempenius et al. | |
| 3,876,806 A | 4/1975 | Hempenius et al. | |
| 4,107,334 A | 8/1978 | Jolly | |
| 4,293,571 A | 10/1981 | Olofsson et al. | |
| 4,585,757 A | 4/1986 | Pang et al. | |
| 4,687,739 A | 8/1987 | Sugisawa et al. | |
| 4,687,840 A | 8/1987 | Pang et al. | |
| 4,980,164 A | * 12/1990 | Manfredi et al. ......... | 424/93.45 |
| 5,238,921 A | 8/1993 | Maruyama et al. | |
| 5,314,873 A | 5/1994 | Tomita et al. | |
| 5,409,718 A | 4/1995 | Klaver et al. | |
| 5,418,218 A | 5/1995 | Wilber | |
| 5,466,472 A | 11/1995 | Kuma et al. | |
| 5,486,461 A | 1/1996 | Nielsen | |
| 5,547,687 A | 8/1996 | Outinen et al. | |
| 5,618,689 A | 4/1997 | McCarthy et al. | |
| 5,656,268 A | 8/1997 | Sorodsky | |
| 5,766,940 A | * 6/1998 | Yamamoto ............... | 435/320.1 |
| 6,214,585 B1 | 4/2001 | Kwon et al. | |
| 6,221,423 B1 | 4/2001 | Cho et al. | |
| 6,372,282 B1 | 4/2002 | Edens et al. | |
| 2002/0132288 A1 | 9/2002 | Swamylingappa et al. | |
| 2002/0182301 A1 | 12/2002 | Draaisma et al. | |
| 2003/0027769 A1 | 2/2003 | Scialdone et al. | |
| 2003/0040475 A1 | 2/2003 | Toba et al. | |
| 2003/0072863 A1 | 4/2003 | Hayasawa et al. | |

FOREIGN PATENT DOCUMENTS

| | | |
|---|---|---|
| FR | 5 528 A1 | 11/1967 |
| JP | 05-236872 A1 | 9/1993 |
| JP | 05-292947 A1 | 11/1993 |
| JP | 07-255467 A1 | 10/1995 |
| JP | 09-002959 A1 | 1/1997 |
| JP | 03-251159 A1 | 11/1997 |
| JP | 10-146157 A1 | 6/1998 |
| JP | 11-239476 A1 | 9/1999 |
| JP | 2000-197469 A1 | 7/2000 |
| WO | WO-01/68113 A1 | 9/2001 |
| WO | WO-01/68114 A1 | 9/2001 |

OTHER PUBLICATIONS

Yamamoto et al., Isolation and characterization of a plasmid from *Lactobacillus helveticus* CP53, Biosci Biotech Biochem 60(12):2069–2070, 1996.*

Karine Thoreux, et al., "Modulation of proliferation, second messenger levels, and morphotype expression of the rat intestinal epithelial cell line IEC–6 by fermented milk", J–Dairy–Science, Jan. 1996, vol. 79–pp. 33–43.

Jiang Hanqing, et al., "Preliminary Research on the Adjustment of Intestinal Dysbacteriosis by *Bifidobacterium* and *Lactobacillus* in Rats", 1995, pp. 32–34.

Chuanbin Wang, et al., "Screening and Studying on Biological Characteristics of Lactobacilli of Animal Origin", Journal of Jiangsu Agricultural College, Dec. 3, 1996, vol. 18, No. 1, pp. 1–5.

Naoyuki Yamamoto et al., "Isolation and characterization of a plasmid from *Lactovacillus helveticus* CP53", Bioscience, Biotechnology, and Biochemistry, Dec. 1996, vol. 60, pp. 2069–2070.

Chandan, R.C., "Enhancing Market Value of Milk by Adding Cultures", J. Dairy Sci., vol. 82, pp. 2245–2256 (1999).

Kontula, P., et al., "The Effect of Lactose Derivatives on Intestinal Lactic Acid Bacteria", J. Diary Sci., vol. 82, pp. 249–256 (1999).

(Continued)

*Primary Examiner*—Robert A. Wax
*Assistant Examiner*—Rosanne Kosson
(74) *Attorney, Agent, or Firm*—Darby & Darby

(57) ABSTRACT

An agent for relieving intestinal disorders which contain live cells of a strain belonging to *Lactobacillus helveticus*. This strain is preferably characterized by a resistance to a specific bile acid, adhesiveness to intestinal epithelial cells, etc. A method of controlling intestinal functions which involves the step of administering such a medicine to a subject with a need for the control of intestinal functions. When administered to humans or the like, these agents exert effects of elevating defecation frequency, etc., thereby efficaciously improving the intestinal environment.

3 Claims, No Drawings

OTHER PUBLICATIONS

Alander, Minna, et al., "Persistence of Colonization of Human Colonic Mucosa by a Probiotic Strain, *Lactobacillus rhamnosus* GG, after Oral Consumption", Applied and Environmental Microbiology, Jan. 1999, vol. 65, No. 1, pp. 351–354.

Biosciences and Industry, Susumu Maruyama, "Production of Hypotensive Peptides from Food Protein", 47 No. 11, 38–42, 1989. (with partial translation).

Japan Fermentation Engineering Society, Susumu Maruyama, et al. "Production of Peptide Inhibitors of the Renin–Angiotensin System from Maize Protein", p. 23, 1988.

Japanese Society for Bioscience, Biotechnology and Agrochemistry, Susumu Maruyama, et al., "Angiotensin Converting Enzyme Inhibitory Effect and Hypotensive Effect of Peptides from Repeat Sequence Region of Corn Seed Protein", p. 8, 1989.

Japan Nutrition and Food Society, Shinsuke Miyoshi, et al., "Hypotensive Effect of Enzymolytic Product of Maize Protein on SHR", p. 113, 1989.

Journal of Japan Agricultural Chemistry Society, Shinsuke Miyoshi, et al., "Angiotensin Converting Enzyme Inhibitory Effect of Peptides Derived from Maize Protein", 64(3), 555, 1990. (translation).

Antonie van Leeuwenhoek, "The Proteolytic Systems of Lactic Acid Bacteria," 70: 187–221. 1996.

* cited by examiner

MEDICINES FOR RELIEVING INTESTINAL DISORDERS

FIELD OF ART

The present invention relates to an agent for relieving intestinal disorders.

BACKGROUND ART

It is known that a variety of microorganisms live and form microorganic flora in an intestinal tract of humans and animals. Such microorganisms are classified into harmful microorganisms that give harmful effects to the host, and beneficial microorganisms that give beneficial effects to the host. These microorganisms keep symbiotic or antagonistic relationship. The harmful microorganisms may be those which produce harmful products such as ammonia, hydrogen sulfide, and amines to place an excessive burden on liver function, and those which relates to carcinogenesis. The harmful microorganisms may include genus *Clostridium*.

Beneficial effects that are given to the host through improvement of intestinal flora may include a variety of effects that will lead to good intestinal environment which is necessary for the host to maintain a healthy life, such as (1) amelioration of gastrointestinal condition such as diarrhea or constipation, (2) prevention of cancer and improvement of infection resistivity through activation of immune system, and (3) suppression of metabolic production of, e.g. harmful enzymes, by the harmful microorganisms. Effective use of the microorganic flora for the health of the host is the idea of so-called probiotics.

There are some proposal for definition of probiotics, such as "a microorganism and a substance that give beneficial effect to a host through control of intestinal flora" (Parker, R. B: An. Nutr. Health, 29, 4–8 (1974)), "a live microorganism that gives beneficial effect to a host by improvement of balance of intestinal florae" (Fullar, R.: J. Appl. Bacteriol., 66, 365–378 (1989)), "a strain of or mix-cultured bacteria that give a beneficial effect to a host by amelioration of factors relating to balance of intestinal florae in the host" (Havenaar, R. and Huis in't Veld, J. H. J.: A general view, In The Lactic Acid Bacteria in Health and Disease/Wood, B. J. B. ed., pp.151–170 (1992) Elsevier, London), "live bacteria and substances promoting proliferation of such bacteria that give a beneficial effect to inherent flora of not only animals but also plants and foods" (Fullar, R.: Probiotics: Their Development and Use, In Old Herborn University Seminar Monograph 8/van der Waaij, D., Heidt, P. J. and Rush, V. C. eds., pp.1~8 (1995) Institute for Microbiology and Biochemistry, Herborn-Dill) (see The Japanese Journal of Nutrition and Dietetics Vol.55 No.4 p167–177: 1997). In any case, a substance that is called probiotics has a function of relieving intestinal disorders.

It is reported that some of lactic acid bacteria have such probiotic properties. Specifically, it is known that some strains of *Lactobacillus bulgaricus*, *Streptococcus thermophilus*, *Lactobacillus acidophilus*, various bifidobacteria, *Lactobacillus casei*, and *Lactobacillus gasseri* have probiotic properties. More specifically, it is known that *Lactobacillus plantarum* 299DSM6596, *Lactobacillus casei* ssp. rhamnosus 271DSM6595 (Japanese Patent No. 2742962 B), *Lactobacillus acidophilus* PN-RI-2-4 (JP-P-H5-292947 A), *Lactobacillus acidophilus* F-133 (Japanese Patent No.3052208 B), bifidobacteria BB536, and *Lactobacillus casei* Shirota strain have probiotic properties.

Particularly, as to the lactic acid bacteria of genus *Lactobacillus*, *L. acidophilus*, *L. agilis*, *L. aviarius*, *L. amylovorus*, *L. brevis*, *L. casei*, *L. crispatus*, *L. delbrueckii* subsp. *bulgaricus*, *L. gallinarum*, *L. gasseri*, *L. johnsonii*, *L. murinus*, *L. hamsteri*, *L. intestinalis*, *L. plantarum*, *L. reuteri*, *L. ruminis*, and *L. salivarius* are at present recognized as probiotics (probiotics A Critical Review: Gerald W. Tannock (1997) p47).

By the way, it is reported that (1) *Lactobacillus helveticus* has high proteolytic activity and thus has high peptide productivity, and (2) a *Lactobacillus helveticus*-fermented milk has an hypotensive effect (Japanese Patent No.3028411 B). Therefore, it is known that an extracellular product obtained by fermenting a milk with *Lactobacillus helveticus* may be used as lactic acid fermented milk material with suppressed lactic acid acidity (JP-P-H10-99018 A), stimulant for interferon production (JP-P-S57-1237 A), and lipid metabolism improver (JP-P-H10-229841 A). However, it is not known that the live bacterial cells of *Lactobacillus helveticus* may be administered to hosts such as humans for use as an agent for relieving intestinal disorders having a probiotic function.

DISCLOSURE OF THE INVENTION

The object of the present invention is to provide an agent for relieving intestinal disorders that, when administered to a subject such as a human, leads to effects such as increased frequency of defecation and is therefore useful for improving the intraintestinal environment.

According to the present invention, there is provided an agent for relieving intestinal disorders comprising live bacterial cells of a strain belonging to *Lactobacillus helveticus*.

According to the present invention, there is also provided a method for controlling intestinal function comprising the step of administering to a subject in need thereof an effective amount of the agent for relieving intestinal disorders.

EMBODIMENTS OF THE INVENTION

The agent for relieving intestinal disorders of the present invention contains live bacterial cells of a strain belonging to *Lactobacillus helveticus*.

The strain belonging to *Lactobacillus helveticus* is preferably resistant against bile acid. Specifically, the minimum growth inhibitory concentration of dry solid bile for the strain in a bile acid resistivity test may preferably be 0.8% or more, and more preferably 1.3% or more.

The minimum growth inhibitory concentration of the dry solid bile is the minimum concentration of the dry solid bile at which concentration the bile can inhibit growth of the strain. Specifically, the minimum growth inhibitory concentration may be measured by preparing a liquid medium in which the strain belonging to *Lactobacillus helveticus* can grow (e.g., MRS medium), adding a variety of concentrations (e.g., 0, 0.05, 0.1, 0.3, 0.5, 1.0, 1.5 and 2.0%) of dry solid bile to the medium, culturing the strain in each medium, measuring turbidity (e.g., at 650 nm) by e.g., absorptiometer after the lapse of certain periods of time (e.g., 0, 4, 8 and 12 hours) to determine specific growth rate (OD/time) at the logarithmic growth phase, and calculating the concentration of the dry solid bile at which the specific growth rate becomes zero by extrapolation of the relationship between the dry solid bile concentration and the specific growth rate. The dry solid bile may specifically be Bacto-oxgall (product name, manufactured by Difco Laboratories).

The strain belonging to *Lactobacillus helveticus* preferably has adhesiveness of $2.8 \times 10^6$ cells/well or more, and preferably $4.5 \times 10^6$ cells/well or more to a monolayer culture of Caco-2 cells in an intestinal tract epithelium cell adhesiveness test in a cylindrical well having a bottom surface area of 1.8 cm$^2$.

The adhesiveness to the intestinal epithelium cells may specifically be tested, for example, in accordance with the Greene and Klaenhammer's method (Greene, J. D. and Klaenhammer, T. R. Applied and Environmental Microbiology 60, 4487–4494 (1994)). More specifically, for example, 1 ml of cultured liquid containing $1\times10^5$ cells/ml of Caco-2 cells may be poured in a cylindrical well having the bottom surface area of 1.8 cm$^2$, and cultured until a monolayer is formed. Number of the cells of the strain that can adhere to the monolayer of the cultured Caco-2 cells per well may be measured. A strain exhibiting cell number that is not less than the aforementioned preferable number may preferably used.

The strain belonging to *Lactobacillus helveticus* may preferably be those which exhibits fecal recovery in humans of $4.0\times10^7$ cells or more following administration of the strain at the dose of $1.0\times10^{11}$ cells.

The amount of the cells of the strain from the collected feces may be measured by the following method: the strain is made resistant against an antibiotic such as rifampicin in accordance with an ordinary method; the resistant bacteria are administered to a human subject; the feces of the subject is collected after the administration; and the number of the bacterial cells in the feces is counted utilizing the antibiotic resistivity. The amount of the strain in the collected feces may also be measured by detecting genes derived from the strain in the feces in accordance with an ordinary method.

As the strain belonging to *Lactobacillus helveticus*, a variety of strains such as *Lactobacillus helveticus* CP53 strain (International Patent Organism Depositary of National Institute of Advanced Industrial Science and Technology, deposition number FERM BP-5770) maybe used. *Lactobacillus helveticus* CP53 strain is particularly preferable.

*Lactobacillus helveticus* CP53 strain has been deposited at National Institute of Bioscience and Human-Technology Agency of Industrial Science and Technology (which is at present called International Patent Organism Depositary of National Institute of Advanced Industrial Science and Technology) on Jan. 11, 1996 as the deposition number FERM BP-5770, and is now publicly available.

The formulation of the present agent for relieving intestinal disorders is not particularly limited and may be any of solids such as powders, granules and tablets; and fluids such as pastes, gels and liquids.

The amount of the live bacterial cells of the strain in the agent for relieving intestinal disorders of the present invention is not particularly limited. However, the amount may preferably be those which enables ingestion of $1.0\times10^{11}$ or more of the live bacterial cells at one administration. Specifically, the content of the live bacteria may be $1.0\times10^6$ cells/g to $1.0\times10^{11}$ cells/g, and preferably $1.0\times10^8$ cells/g to $1.0\times10^{11}$ cells/g.

Although the method for producing the agent for relieving intestinal disorders may not be limited, the agent may be produced by fermenting milk with a strain belonging to *Lactobacillus helveticus*, to obtain live bacterial cells of the strain belonging to *Lactobacillus helveticus*. The milk may be animal milk such as cow's milk, horse milk, goat milk and sheep milk; and vegetable milk such as soybean milk. The fermentation temperature may be 20° C. to 50° C., and preferably 30° C. to 45° C. The fermentation time may preferably be 3 to 48 hours, and preferably 6 to 24 hours. The fermented product itself obtained by fermentation of the milk with the strain belonging to *Lactobacillus helveticus* may be utilized as the agent for relieving intestinal disorders of the present invention. The fermented product may further be admixed with other materials such as other additives and food materials, and optionally processed to be in a form such as powders, granules and tablets, for use as the agent for relieving intestinal disorders of the present invention. Alternatively, the live bacterial cells of the strain belonging to *Lactobacillus helveticus* cultured in accordance with the aforementioned fermentation or other methods may be collected from the medium, and the collected bacteria itself may be utilized as the agent for relieving intestinal disorders of the present invention. The collected bacteria may further be admixed with other materials such as other additives and food materials, and optionally processed to be in a form such as powders, granules and tablets, for use as the agent for relieving intestinal disorders of the present invention.

The subject to which the agent for relieving intestinal disorders of the present invention is administered may be animals such as mammals including humans, without limitation.

The dose of the agent for relieving intestinal disorders of the present invention may be $1.0\times10^{11}$ cells in terms of number of the live bacterial cells per one day in the case of human. The agent may be administered at a time or a plurality of times.

When the agent for relieving intestinal disorders of the present invention is administered to an animal including human, it may result in relief of intestinal disorders represented by increased frequency of defecation and amount of feces.

The agent for relieving intestinal disorders of the present invention gives an effect such as the increased frequency of defecation when administered to an animal such as a human, and is therefore useful for improving the intraintestinal environment.

EXAMPLES OF THE INVENTION

The present invention will be explained more in detail with reference to the Examples. However, the present invention is not limited thereto.

In the following Examples, adhesiveness to Caco-2 cells was measured as follows:

Test of Adhesiveness to Caco-2 Cells

Adhesiveness to Caco-2 cells was measured in accordance with Greene and Klaenhammer's method. Caco-2 cells purchased from American Type Culture Collection (HTB-37) in MEM medium (Gibco BRL) containing 5% calf serum albumin (Gibco Bethesda Reserarch Laboratory) that had been inactivated by heating at 55° C. for 30 minutes were cultured at 37° C. in 5% $CO_2$ incubator. 1 ml of the cultured liquid containing $1\times10^5$ cells/ml was transferred to a cultivation plate having 24 wells (manufactured by Sumitomo Bakelite Co., Ltd., trade name MS-80240). The medium was exchanged every 48 hours until the cells form a monolayer. 0.1 ml of 20% glutaraldehyde (Wako Pure Chemical Industries, Ltd.) was added for fixing the cells to the culturing plate. The plate was left stand for 30 minutes and washed two times with PBS. 0.5 ml ($1\times10^9$ cells) of a liquid containing cells to be tested that had been isotope-labeled were added. After culturing at 37° C. for one hour, free cells were removed by washing the plate three times. 200 μl of 1% SDS, 1N NaOH was added and left stand for 30 minutes. The mixture of the Caco-2 cell and the bacterial cells were recovered from the wells, and suspended in a scintillator cocktail (Scintisol EX-H, Wako Pure Chemical Industries, Ltd.) and radio activity thereof was measured with a liquid scintillation counter LSC-900 (Aloka Co., Ltd.). The number of the cells adhered was calculated on the basis of specific radioactivity of the cells that had previously been counted. The measurement was performed twice and average was taken as the result.

Example 1

Lactobacillus Helveticus CP53 Strain

Lactobacillus helveticus CP 53 strain is known to have therein a plasmid DNA, pCP53 (Yamamoto, N. and Takano, T.: Biosci. Biotech. Biochem., 60 (12), 2069–2070 (1996)). Lactobacillus helveticus CP53 strain was cultured in a variety of MRS mediums each containing different concentration of solid bile powders (Bacto-oxgall (Difco)) for measuring minimum growth inhibitory concentration. The minimum growth inhibitory concentration was found to be 1.31%. Adhesiveness to Caco-2 cells was also measured and confirmed to be $4.5 \times 10^6$ cells/well or more.

Conferring Rifampicin Resistance

For recovery from feces in the ingestion test, resistance against the antibiotic rifampicin was conferred to CP53 strain in accordance with an ordinary method. The CP53 strain was spread on a MRS plate medium containing 100 μg/ml of rifampicin. The rifampicin-resistant strain that grew on this plate medium was selected as CP53-R strain.

Properties of CP53-R Strain

CP53-R strain was subcultured seven times in MRS medium that did not contain rifampicin. The subcultured strain was cultured in a variety of MRS mediums each containing different concentration of solid bile powders for measuring the minimum growth inhibitory concentration, which was found to be 0.86%. Adhesiveness to Caco-2 cells was also measured and confirmed to be $2.8 \times 10^6$ cells/well or more. Further, this subcultured strain was confirmed to contain the plasmid pCP53.

Ingestion-Recovery Test on Volunteers

CP53-R strain cultured in MRS medium (Difco) was collected by centrifugation, washed twice with PBS, and suspended in cow's milk at a concentration of $1 \times 10^{11}$ cells/100 ml. The milk suspension containing CP53-R strain was employed as an ingestion sample for the ingestion-recovery test. Seven healthy subjects at the age of 25 to 41 drunk 100 ml of the ingestion sample at once. All of feces defecated from the subjects within 5 days from the ingestion were collected. Frequency of defecation, and amount and hardness of feces from each subject after administration of the ingestion sample were recorded. The results are shown in Table 1. The collected feces was immediately frozen and stored at 4° C., and the following analyses were performed on the next day.

Survival of L. Helveticus

Utilizing the MRS plate medium containing rifampicin, number of live bacterial cells having rifampicin resistance in the feces samples was counted. The number of bacterial cells contained in all of the collected feces was calculated. As a result, average number of recovered bacterial cells per person was $1.2 \times 10^8$ cells. It was confirmed that all of the bacteria survived on the MRS plate medium containing rifampicin had the plasmid pCP53, i.e., they were CP53-R strain.

Intraintestinal Growth of L. Helveticus

CP53 strain cells were washed twice with PBS, and subjected to alkaline bacteriolysis with 10 mg/ml lysozyme (Seikagaku Corporation) and 1 mg/ml of mutanolysin (Seikagaku Corporation), to prepare pCP53 plasmid DNA. The DNA was then purified by high speed centrifugation with CsCl density gradient, and radioisotope-labeled with Random Primer DNA Labeling Kit ver 2.0 (Takara Bio Inc.) and [α-$^{32}$P] dCTP (222 TBq/mmol, New Life Products Inc.), to obtain a $^{32}$P radio-labeled pCP53 plasmid DNA.

In a centrifugation tube of 15 ml volume, 5 ml of 30% sucrose solution, 2 ml of 20% sucrose solution and 2 ml of 10% sucrose solution were calmly piled up, to obtain a step density gradient sucrose solution. The feces sample collected from the subjects was diluted 20 times (w/w) and suspended in a distilled water, and 0.5 ml of the suspension was laid on the step gradient sucrose solution. The laid liquids were centrifuged for five minutes at 1500×g. 10% and 20% sucrose fractions were collected, and washed twice with sterilized water. A DNA fraction was obtained by the Leenhouts' method (Leenhouts, K. J., Kok, J., and Venema, G. (1990) Appl. Environ. Microbiol., 56, 2726–2735). The obtained DNA fraction was dissolved in 10 mM Tris Cl pH 8.0, 1 mM EDTA. 10 and 100 times dilutions of the solution with the same buffer were also prepared. These DNA fractions were heated for three minutes and 10 μl each thereof was dot-blotted on a nylon membrane (Hybond-N$^+$, Amersham Pharmacia Biotech). The blotted nylon membrane was washed with distilled water and dried, to fix DNA.

To the fixed DNA on the membrane, the aforementioned radio-labeled pCP53 plasmid DNA was hybridized in accordance with Maniatis' method (Maniatis, T., Frish, E. F. and Sambrook, J. (1987) Molecular Cloning; a laboratory manual. Cold Spring Harbor Laboratory, Cold Spring Harbor). Upon hybridization, formaldehyde and chromosomal DNA derived from a variety of bacteria in separately prepared feces that did not contain CP53 strain were added thereto at 50% (w/w) and 10 μg/ml, respectively, for avoiding non-specific hybridization.

For quantification of pCP53 plasmid, the membrane after hybridization was subjected to autoradiography, and each sample dot portion (0.5×0.5 mm) was cut off. Radio activity of the taken dot portions were measured with a liquid scintillation counter LSC-900 (Aloka Co., Ltd.).

Separately, for obtaining a calibration curve, $8.5 \times 10^3$ to $2.0 \times 10^5$ cells of CP53 strain was mixed with feces to prepare feces samples, which were subjected to the aforementioned DNA fraction preparation, dot-blotting and reaction with radio-labeled pCP53 plasmid DNA. The bound radio activity was in linear proportion to number of CP53 strain cells that had been mixed with feces in a range of $8.5 \times 10^3$ to $2.0 \times 10^5$ cells/g (weight of feces), and a calibration line was thus obtained. With this calibration line, amount of CP53 strain cells in the feces samples from the ingestion-recovery test subjects was determined in a range of $1 \times 10^4$ to $2.0 \times 10^5$ cells/g (weight of feces)

As a result, CP53 strain cells were found in all of the feces samples collected from the seven subjects. Number of total CP53 strain cells in all of feces samples from each subject was $4.0 \times 10^9$, $1.0 \times 10^9$, $3.0 \times 10^9$, $1.0 \times 10^9$, $1.0 \times 10^9$, $4.0 \times 10^7$ and $4.0 \times 10^8$ cells, respectively. In each subject, CP 53 strain was found in all of the feces samples of the first, second and third defecation after taking the ingestion sample. The amounts of CP53 strain cells in the feces samples of the third and subsequent defecation were greater than that of the first and second defecation. This fact suggests that CP53 strain can grow and proliferate in the intestinal tract even it can hardly grow in feces.

Feces from subjects who had not ingested CP53-R live bacteria was also taken as feces sample, and DNA fractions were prepared therefrom in the same way as the above. These DNA fractions and purified pCP53 plasmid DNA were dot-blotted and reacted with the radio-labeled pCP53 plasmid DNA in the same way. As a result, the radio-labeled pCP53 plasmid DNA strongly reacted with purified pCP53 plasmid, but did not react at all with the DNA fractions derived from the feces from the subjects who had not ingested CP53-R live bacteria.

Comparative Example 1

Example 1 was followed except that the ingestion sample was heat-sterilized before administration to the subjects. Frequency of defecation, and amount and hardness of the feces of each subject were recorded. The results are shown in Table 1.

TABLE 1

|  | Example 1 | Comp. Example 1 |
| --- | --- | --- |
| Frequency of defecation (times/5 days) | 5.6 ± 1.9* | 4.6 ± 1.6 |
| Amount of feces (ml/day) | 140 ± 57 | 130 ± 48 |
| Hardness (as to the first feces after intake of the ingestion sample)[a] | 1.9 ± 0.38 | 1.9 ± 0.69 |

*Significant compared to Comparative Example 1 (p < 0.1, Wilcoxon's signed rank test)
[a] Evaluated in three degrees: 1; hard, 2; normal, 3; soft. Average was calculated.

Formulation Example 1

1.485 kg of skim milk powders (manufactured by Yotsuba Inc.) were dissolved in 8.415 kg of purified water. The solution was heat-sterilized at 95° C. for 30 minutes and then quickly cooled down to 32° C. To the recombined and sterilized skim milk was aseptically added 0.1 kg of bulk starter of *Lactobacillus helveticus* CP 53 strain. The mixture was thoroughly stirred and fermented at 32° C. for 16 to 20 hours. The fermentation was terminated when the acidity of the fermented milk (weight percentage of lactic acid) reached in a range of 1.5 to 2.1. After finishing the fermentation, the fermented milk was quickly cooled down to 10° C. or less to obtain 10 kg of fermented milk material. At that time, number of live CP53 strain cells per 1 g reached at least 1.5 billion.

0.8 kg of granulated sugar powders and 0.03 kg of pectin YM115-H powders (manufactured by Copenhagen Pectin) were mixed and dissolved in 4.17 kg of purified water warmed at 70° C. The solution was heat-sterilized at 95° C. for several seconds and then quickly cooled down to 10° C. or less to obtain 5 kg of sterilized sugar-stabilizer solution.

5 kg of the fermented milk material was aseptically added to 5 kg of the sterilized sugar-stabilizer solution and the mixture was aseptically homogenized with a laboratory homogenizer (type: 15M-8BA, manufactured by APV Gaulin) at the homogenizing pressure of 15 MPa and processing flow rate of 2.5 L/min, to obtain 10 kg of dairy lactic acid bacteria beverage bulk. The dairy lactic acid bacteria beverage bulk was aseptically poured into polystyrene bottles of 200 g size. The bottles were heat-sealed with polyethylene-aluminum laminated films, to obtain dairy lactic acid bacteria beverage products having quality preservation period of 14 days in refrigerator (10° C. or less).

The obtained product contained at least 750 million CP53 strain cells per 1 g. When preserved at 10° C. or less, the product was able to maintain 500 million live bacterial cells per 1 g even at 14 days after production. Therefore, drinking 200 g of the product results in ingestion of 100 billion or more of live CP53 bacterial cells.

Formulation Example 2

0.180 kg of skimmed soybean milk powders (trade name "Soyafit 2000" manufactured by Fuji Oil Co., Ltd.) was dissolved in 1.738 g of purified water, which was then admixed with 0.080 kg of lactose and 0.002 kg of yeast (trade name "Ebios P2G" manufactured by Asahi Breweries, Ltd.) and stirred. The mixture was sterilized at 95° C. for several seconds and then quickly cooled down to 25° C. To the recombined and sterilized skim soybean milk thus obtained was aseptically added 0.060 kg of bulk starter of *Lactobacillus helveticus* CP53 strain. The mixture was thoroughly stirred and fermented at 37° C. for 24 to 48 hours with stirring at 100 rpm. The fermentation was terminated when the acidity of the fermented milk reached in a range of 1.5 to 2.1. After finishing the fermentation, the fermented soyabean milk was quickly cooled down to 10° C. or less to obtain 2 kg of fermented soyabean milk material. At that time, number of live CP53 bacterial cells per 1 g reached at least 2 billion.

0.44 kg of granulated sugar powders and 0.015 kg of pectin YM115-H powders (manufactured by Copenhagen Pectin) were mixed and dissolved in 3.56 kg of purified water warmed at 70° C. The solution was heat-sterilized at 95° C. for several seconds and then quickly cooled down to 10° C. or less to obtain 4 kg of sterilized sugar-stabilizer solution.

2 kg of the fermented soyabean milk material was aseptically added to 4 kg of the sterilized sugar-stabilizer solution and the mixture was aseptically homogenized with a laboratory homogenizer (type: 15M-8BA, manufactured by APV Gaulin) at the homogenizing pressure of 15 MPa and processing flow rate of 2.5 L/min, to obtain 6 kg of soyabean lactic acid bacteria beverage bulk. The soyabean lactic acid bacteria beverage bulk was aseptically poured into polystyrene bottles of 200 g size. The bottles were heat-sealed with polyethylene-aluminum laminated films, to obtain soyabean lactic acid bacteria beverage products having quality preservation period of 14 days in refrigerator (10° C. or less).

The obtained product contained at least 660 million CP53 strain cells per 1 g. When preserved at 10° C. or less, the product was able to maintain 500 million live bacterial cells per 1 g even at 14 days after production. Therefore, drinking 200 g of the product results in ingestion of 100 billion or more of live CP53 bacterial cells.

What is claimed is:

1. A method for controlling intestinal function, wherein the control is increased frequency of defecation and amount of feces, comprising the step of administering to a subject in need thereof an effective amount of an agent comprising live bacterial cells of a strain belonging to *Lactobacillus helveticus*, wherein the minimum growth inhibitory concentration of dry solid bile for said strain is at least 0.8% as determined by a bile acid resistivity test for said strain, wherein said strain has an adhesiveness of $2.8 \times 10^6$ cells/well or more to a monolayer culture of Caco-2 cells in a cylindrical well having a bottom surface area of 1.8 cm$^2$ in an intestinal tract epithelium cell adhesion test, and wherein said strain has a fecal recovery in humans of $4.0 \times 10^7$ cells or more following administration of the strain at a dose of $1.0 \times 10^{11}$ cells.

2. The method of claim 1, wherein said strain is *Lactobacillus helveticus* CP53 strain (International Patent Organism Depositary of National Institute of Advanced Industrial Science and Technology, deposition number FERM BP-5770).

3. The method of claim 1, wherein said agent is administered at a dose of $1.0 \times 10^{11}$ cells in terms of number of the live bacterial cells per one day.

* * * * *